United States Patent
Nair et al.

(10) Patent No.: US 7,531,701 B2
(45) Date of Patent: May 12, 2009

(54) ALLYLOXYTRIFLUOROPROPENES

(75) Inventors: Haridasan K. Nair, Willamsville, NY (US); Rajiv R. Singh, Getzville, NY (US); Gregory J. Shafer, Buffalo, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 11/900,081

(22) Filed: Sep. 10, 2007

(65) Prior Publication Data

US 2008/0064837 A1    Mar. 13, 2008

Related U.S. Application Data

(60) Provisional application No. 60/843,934, filed on Sep. 12, 2006.

(51) Int. Cl.
*C07C 43/17* (2006.01)
*C07C 41/01* (2006.01)

(52) U.S. Cl. ...................... 568/674; 568/685
(58) Field of Classification Search .......... None
See application file for complete search history.

(56) References Cited

U.S. PATENT DOCUMENTS

| | | | | |
|---|---|---|---|---|
| 4,433,180 | A | * | 2/1984 | von Werner .......... 568/684 |
| 6,255,535 | B1 | * | 7/2001 | Schulz et al. .......... 568/596 |
| 6,930,159 | B1 | | 8/2005 | Morita et al. .......... 526/245 |

FOREIGN PATENT DOCUMENTS

| | | |
|---|---|---|
| DE | 3138235 | 4/1983 |
| JP | 06 025403 | 2/1994 |

OTHER PUBLICATIONS

Nobuo et al., abstract of JP 58-152830, published Sep. 1983.*

Crivello et al; "*Chemoselective Hydrosilation. I. Synthesis and Photopolymerixation of 1-Propenyl Ether Functionalized Siloxanes*"; Polymer Chemistry, J. Polymer Sci. A:Polym. Chem. (1995) 33(14); pp. 2415-2423.

Sangermano et al; "*Synthesis of New Fluorinated Allyl Ethers for the Surface Modification of Thiol-Ene Ultraviolet-Curable Formulations*"; J. Polym. Sci., Part A, Polym. Chem., 2002, 40; pp. 2583-2590.

Howell et al; "*New Derivatives of Poly-Hexafluoropropylene Oxide from the Corresponding Alcohol*"; J. Fluorine Chem., (2005); pp. 126, 281-288.

Hong et al; "*A Novel and Convenient Synthesis of (Z)-3,3,3-Trifluoropropenyl Alkyl Ethers and CF3-Substituted Propyl Acetals as Versatile CF3-Containing Building Blocks*"; Chem Commun., (1996); pp. 57-58.

Crivello et al; "*Transition Metal-Catalyzed Tandem Isomerization and Cationic Polymerization of Allyl Ethers. I. Discovery and Scope*"; J. Polymer Sci. S: Polym. Chem. (1997) 35; pp. 1593-1604.

* cited by examiner

*Primary Examiner*—Rosalynd Keys
(74) *Attorney, Agent, or Firm*—Erkia S. Wilson

(57) ABSTRACT

A process for the preparation of an allyloxytrifluoropropene derivative of the formula $CF_3CH=CR^1(OCH_2CR=CH_2)$ wherein $R^1$ is hydrogen, fluoro, or an allyloxy group represented by the formula $—OCH_2CR=CH_2$ wherein R is hydrogen or methyl including contacting (I) a compound represented by the formula $CF_3CH=CR^2R^3$ wherein $R^2$ is selected from the group consisting of hydrogen, chloro, and fluoro and wherein $R^3$ is chloro or fluoro; and (ii) an allyl alcohol derivative of the formula $HOCH_2CR=CH_2$ wherein R is selected from the group consisting of: hydrogen and methyl; wherein the contacting is carried out in the presence of a base and optionally a solvent at a temperature and length of time sufficient to produce the allyloxytrifluoropropene derivative. A process for the preparation of polymers of the allyloxytrifluoropropene derivatives is also provided.

18 Claims, No Drawings

ALLYLOXYTRIFLUOROPROPENES

CROSS-REFERENCE TO A RELATED APPLICATION

The present application claims priority from U.S. Provisional Application No. 60/843,934, filed Sep. 12, 2006, the contents of which are incorporated herein by reference in its entirety.

BACKGROUND OF THE INVENTION

1. Field of the Invention

The present invention generally relates to a process for making allyloxytrifluoropropenes and homopolymers and copolymers thereof starting from fluoro olefins. More particularly, the present invention relates to a process for making compounds, such as, $CF_3CH=CHOCH_2CH=CH_2$, $CF_3CH=CFOCH_2CH=CH_2$, $CF_3CH=C(OCH_2CH=CH_2)_2$ and methallyl derivatives thereof from $CF_3CH=CHF$ or $CF_3CH=CF_2$ and allyl or methallyl alcohol.

2. Description of the Prior Art

Compounds containing allyloxy group are typically used as monomers for preparing siloxane polymers or as a $CF_3$ building block. See, for example, *Polymer Chemistry*, (1995) 33(14), 2415-23, *J. Polymer Sci. A: Polym. Chem* (1997) 35, 1593-1604 and *Chem. Commun.*, (1996), 57-58.

Uses of polymers derived from allyl ethers for UV curing, to films on various surfaces, for adhesives, coating, cladding and the like are described in *J. Polym. Sci., Part A, Polym. Chem.*, 2002, 40, 2583-2590.

Allyloxypropene of the formula $CF_3CH_2CFHOCH_2-CH=CH_2$ is used as a monomer for making siloxane polymers, as described in the German Patent DE 3,138,235 A1 and in *J. Fluorine Chem.*, (2005), 126, 281-288.

Relatively little is known about allyloxypropene polymers in general. U.S. Pat. No. 6,930,159 B1 describes some fluorinated allyl ether polymers. However, the structure of monomers used in the preparation of the polymers described in this patent is quite different from the allyloxypropene monomers described in the present invention.

Relatively little is known about allyloxypropenes described by the present invention. The only known example in this group is 1-allyloxy-3,3,3-trifluoropropene of the formula $CF_3CH=CH(OCH_2CH=CH_2)$ which is made from $CF_3CBr=CH_2$ with a base and catalytic amount of water. This reaction proceeds by an elimination-addition mechanism through the formation of trifluoromethylpropyne as an intermediate followed by the addition of allyl alcohol to the so formed trifluoromethylpropyne (See *Chem. Commun.*, (1996), 57-58).

However, large-scale preparation of allyloxytrifluoropropenes using this approach requires the use of $CF_3CBr=CH_2$ as a starting material, which is expensive and cumbersome to manufacture.

Compounds such as $CF_3CH=C(OCH_2CH=CH_2)_2$ with two allyloxy groups and polymers derived therefrom are unknown in the art.

Consequently, there is a need in industry to develop commercially feasible processes for making such compounds and exploring their properties and uses in various applications.

To achieve this objective, the present invention provides a process, which is practical and, as such, it is potentially useful commercially.

SUMMARY OF THE INVENTION

The present invention provides a process for the preparation of an allyloxytrifluoropropene derivative represented by the formula:

$$CF_3CH=CR^1(OCH_2CR=CH_2)$$

wherein:
$R^1$ is selected from hydrogen, fluoro, and allyloxy group represented by the formula:

$$-OCH_2CR=CH_2$$

wherein R is hydrogen or methyl.
The process includes the steps of:
contacting:
(i) a compound represented by the formula:

$$CF_3CH=CR^2R^3$$

wherein $R^2$ is selected from the group consisting of hydrogen, chloro, and fluoro and wherein $R^3$ is chloro or fluoro; and
(ii) an allyl alcohol derivative represented by the formula:

$$HOCH_2CR=CH_2$$

wherein R is hydrogen or methyl;
wherein the contacting is carried out in the presence of a base and optionally a solvent at a temperature and length of time sufficient to produce the allyloxytrifluoropropene derivative.

The present invention further provides wherein the compound represented by the formula $CF_3CH=CR^2R^3$ is selected from the group consisting of $CF_3CH=CHF$, $CF_3CH=CF_2$ and $CF_3CH=CHCl$.

When the compound represented by the formula $CF_3CH=CR^2R^3$ is selected from $CF_3CH=CF_2$ then the contacting is carried out in a ratio of about 1:1 of the compound represented by the formula $CF_3CH=CF_2$ to the allyl alcohol derivative represented by the formula $HOCH_2CR=CH_2$ to produce an allyloxy derivative represented by the formula $CF_3CH=CF(OCH_2CR=CH_2)$ wherein R is selected from the group consisting of: hydrogen and methyl; or the contacting is carried out in a ratio of about 1:2 of the compound represented by the formula $CF_3CH=CF_2$ to the allyl alcohol derivative represented by the formula $HOCH_2CR=CH_2$ to produce an allyloxy derivative represented by the formula $CF_3CH=C(OCH_2CR=CH_2)_2$ wherein R is selected from the group consisting of: hydrogen and methyl.

The present invention further provides allyloxytrifluoropropene derivatives, including compounds of the following formula:

$$CF_3CH=C(OCH_2CH=CH_2)_2;$$

$$CF_3CH=C(OCH_2C(CH_3)=CH_2)_2;$$

$$CF_3CH=CH(OCH_2C(CH_3)=CH_2); \text{ and}$$

$$CF_3CH=CF(OCH_2CR=CH_2);$$

wherein R is hydrogen or methyl.
The present invention still further provides process for preparing a polymer including the step of:
polymerizing:
(iii) an allyloxytrifluoropropene derivative selected from compounds represented by the formula:

$$CF_3CH=CH(OCH_2CR=CH_2);$$

$$CF_3CH=C(OCH_2CR=CH_2)_2;$$

$$CF_3CH=CF(OCH_2CR=CH_2); \text{ and}$$

any mixtures thereof;
wherein R is hydrogen or methyl; and optionally
(iv) an ethylenically unsaturated comonomer;

wherein the copolymerizing step is carried out in the presence of a catalyst, preferably including methylphenylsilane and $Co_2(CO)_8$, under conditions sufficient to produce the copolymer.

The present invention also provides homopolymers and copolymers of these allyloxytrifluoropropene derivatives prepared by the polymerization process according to the present invention.

The process according to the present invention is practical and, as such, it is potentially useful commercially.

These and other benefits of the present invention will become more evident from detailed description of the preferred embodiments that follow.

DETAILED DESCRIPTION OF THE PREFERRED EMBODIMENTS

When $CF_3CH=CF_2$ is reacted with allyl alcohol or methallyl alcohol at 25° C. to 35° C. with catalytic amount of a base, such as, $Cs_2CO_3$, in a polar solvent, quite unexpectedly, the major product formed was the fluoride substitution produce, rather than the expected product of addition to the carbon-carbon double bond, to form $CF_3CH=C(OCH_2—CH=CH_2)_2$ (IA).

Even with only catalytic amount of a base being present, both of the vinylidene fluorines in $CF_3CH=CF_2$ can be replaced by allyloxy group. This is an unknown reaction of vinylidene fluorides and, as such, it is an unexpected reaction.

Temperature appears to play an important role in these reactions. At lower temperatures, such as, for example, at temperatures from about −20° C. to about 5° C., one can predominantly obtain the addition product of the formal $CF_3CH_2CF_2OCH_2—CH=CH_2$ (IC).

In contrast, when a temperature from about 25° C. to about 35° C. is used, the major product formed is $CF_3CH=C(OCH_2—CH=CH_2)_2$ (IA); the minor being $CF_3CH=CF(OCH_2—CH=CH_2)$ (IB) (~5 to 20%) as shown in Scheme 1 below. Thus, under these experimental conditions, only trace amount of the expected addition product (IC) was seen.

This above reactions are depicted in the Scheme 1 below.

This approach is described in greater detail in *Chem. Commun.*, 1996, 57-58 and is depicted in Scheme 2 herein below.

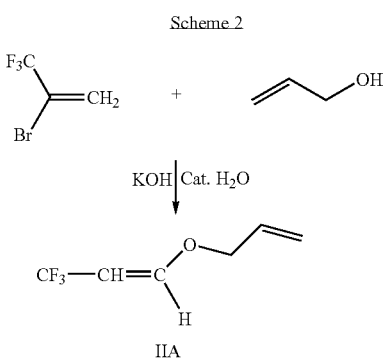

In the present invention, this problem can be overcome by the use of commercially available $CF_3CH=CHF$ with a base, as depicted in Scheme 3 below.

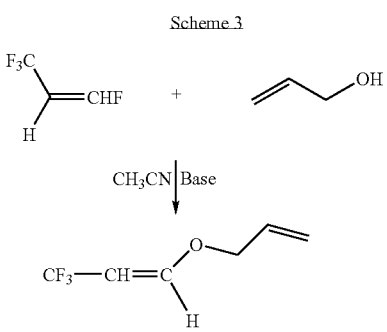

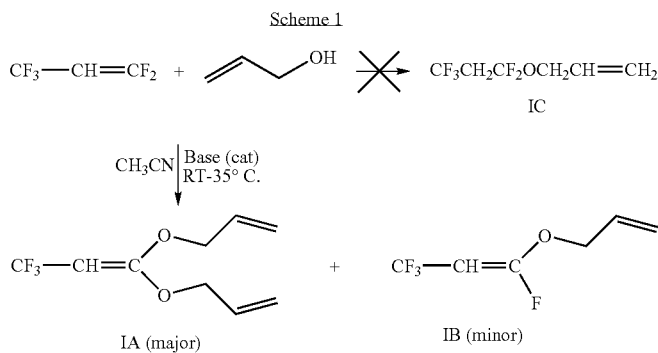

In large scale preparations, the volatiles generated in the reaction can be trapped in a cold trap/scrubber and thereafter neutralized and the HF generated can be neutralized via washing with aqueous NaOH solution.

Alternately, if the exclusive preparation of IA is desired, one can employ two equivalents of base to neutralize the HF generated during the reaction.

As mentioned before, the reparation of Compound IIA $CF_3CH=CH(OCH_2CH=CH_2)$ has been reported in the literature using a method which employs $CF_3CBr=CH_2$ as a starting material.

Alternately, $CF_3CH=CHCl$ can also be used in place of $CF_3CH=CHF$ which is commercially available. Typically, bases such as $Cs_2CO_3$, $K_2CO_3$, and sodium or potassium tertiary butoxide can be used in Schemes 1 and 2.

The starting material $CF_3CH=CHF$ can be made in large scale from commercially available $CF_3CH_2CF_2H$ according to methods described in U.S. Pat. No. 6,548,719 B1. $CF_3CH_2CF_2H$ is produced by and is available from Honeywell International, Inc., Morristown, N.J.

Preferably, $CF_3CH=CF_2$ is formed from $CF_3CH_2CF_2H$ by chlorination followed by dehydrochlorination and $CF_3CH=CHF$ is formed from $CF_3CH_2CF_2H$ by dehydrofluorination.

The step of contacting is carried out at a temperature sufficient to produce the allyoxytrifluoropropene derivative. Contacting is preferably carried out at a temperature of about 25° C. to about 100° C., more preferably about 25° C. to about 50° C., and most preferably about 25° C. to about 35° C.

The step of contacting is carried out at a pressure sufficient to produce the allyoxytrifluoropropene derivative. Contacting is preferably carried out at a pressure of about 0.5 to about 1 atm and most preferably about 1 atm.

The step of contacting is carried out for a length of time sufficient to produce the allyoxytrifluoropropene derivative. Contacting is preferably carried out for a length of time of about 5 minutes to about 300 hours, more preferably about 30 minutes to about 5 hours, still more preferably about 30 minutes to about 2 hours, and most preferably about 2 hours.

The step of contacting is preferably carried out at a temperature from about 25° C. to about 50° C., at a pressure of about 0.5 atm to about 1 atm, and for a length of time from about 30 minutes to about 5 hours.

More preferably, the step of contacting is carried out at a temperature from about 25° C. to about 35° C., at a pressure from about 1 atm, and for a length of time from about 30 minutes to about 2 hours.

The process can be either a batch process or it can be a continuous process.

The reactor can further include a diluent, such as, a solvent or mixture of solvents. Preferably, polar, non-protic solvents, such as, acetonitrile, dimethylformamide (DMF), dimethylsulfoxide (DMSO), are used as the reaction medium. However, other solvents, such as, mono- and di-ethers of glycols, mono- and di-esters thereof, glymes, diglymes, triglymes, and tetraglymes can also be employed.

The process can further include one or more of the following steps:

(1) isolating the product from the reaction mixture by pouring the crude reaction mixture onto cold water at about 5° C. whereby the product separates out the lower layer; and (2) purifying the reaction product via distillation under reduced pressure to obtain the product in substantially pure form.

In operation, preferably at least 10 wt % of the reactants are converted to the product. More preferably, up to at least 80 wt % of the reactants are converted to the product, and most preferably, at least 90 wt % of the reactants are converted to the product. Accordingly, operation of the process of the present invention under high conversion conditions is preferred.

Polymerization can be carried out essentially the same way as the methods known and described in the art, such as, the methods described in *J. Polymer Sci. A: Polym. Chem.* (1997) 35, 1593-1604 and U.S. Pat. No. 6,930,159 B1. Thus, both monomers can be readily polymerized to form homopolymers under standard polymerization conditions known to a person skilled in the art.

Alternatively, these monomers can be also readily polymerized to copolymers if an ethylenically unsaturated comonomer is present.

Depending on the polymerization conditions, the polymers can be obtained as transparent or white powders.

The allyloxytrifluoropropenes according to the present invention are suitable for use as monomers in the preparation of polymers and copolymers, including preparation of coatings, and particularly UV cured coatings.

The following non-limiting examples are illustrative of the various embodiments of the present invention. It is within the ability of a person of ordinary skill in the art to select other variable from amongst the many known in the art without departing from the scope of the present invention. Accordingly, these examples shall serve to further illustrate the present invention, not to limit them.

Experimental Details:

Unless otherwise indicated, all parts and percentages are on a weight basis.

EXAMPLE 1

1,1-Bis-allyloxy-3,3,3-trifluoropropene ($CF_3CH=C(OCH_2CH=CH_2)_2$)

To a stirred mixture of acetonitrile (100 mL), allylalcohol, $CH_2=CHCH_2OH$, (20 g, 0.34 mol) and catalytic amount cesium carbonate (1.5 g, 4.6 mmol) was added, $CF_3CH=CF_2$ (0.40 mol) via a gas sparger. The addition of $CF_3CH=CF_2$ was such that the temperature of the reaction was not more than 36° C. After complete addition (30 minutes), the reaction mixture was stirred for 1 hour, poured into 400 mL cold water, mixed well and the upper layer was separated. Separated organic layer was mixed with water (400 mL), allowed to settle. The lower layer was separated, washed with water (50 ml), dried (MgSO4) and filtered to afford crude product $CF_3CH=C(OCH_2CH=CH_2)_2$. Pure product was obtained on distillation under reduced pressure (50 to 55° C./8-9 mm Hg) as a colorless liquid (25 g, 35% yield).

The structure of the product is consistent with the following spectroscopic data:

GC/MS data: m/e 208 ($M^+$ for $C_9H_{11}F_3O_2$);

$^{19}F$ NMR ($CDCl_3$) $\delta$=−68.6 (3F, d, $J_{HF}$=8 Hz) ppm; and $^1H$ NMR ($CDCl_3$) $\delta$=5.87 (1H, m), 5.71 (1H, m), 5.36-5.09 (4H, m), 4.65 (2H, dt, J=6 and 2 Hz), 3.2 (1H, m), 2.6 (2H, m) ppm.

The other product formed in this reaction is $CF_3CH=CF(OCH_2CH=CH_2)$.

EXAMPLE 2

1-Allyloxy-3,3,3-trifluoropropene ($CF_3CH=CH(OCH_2CH=CH_2)$)

To a stirred mixture of acetonitrile (240 mL), allylalcohol, $CH_2=CHCH_2OH$, (20 g, 0.34 mol) and sodium tertiarybutoxide (34.5 g, 0.36 mol) was added, $CF_3CH=CFH$ via a gas sparger. The addition $CF_3CH=CFH$ was such that the temperature of the reaction was not more than 35° C. After complete addition (about 45 minutes), the reaction mixture was stirred for 1 hour, poured into 400 mL cold water, mixed well and the upper layer was separated. Separated organic layer was mixed with water (400 mL), allowed to settle. The lower layer was separated, washed with water (50 ml), dried ($MgSO_4$) and filtered to afford 42 g product characterized to be $CF_3CH=CHOCH_2CH=CH_2$, which was 86% pure, by GC. Pure product was obtained on distillation under reduced pressure (36 to 42° C./68 mm Hg) to afford the pure product as a colorless liquid (32 g, yield=62%). The ratio of cis- to trans- isomer is 96:2.

The structure of the product is consistent with the following spectroscopic data:

GC/MS data: m/e 152 for M+ (M=$C_6H_7F_3O$);

NMR data for trans: $^{19}$F NMR (CDCl$_3$), δ=−59.1 (3F, m) ppm; and $^1$H NMR (CDCl$_3$) δ=7.03 (1H, dq, overlaps J=12 and 2 Hz), 5.92 (m, 1H), 5.28-5.40 (m, 2H), 5.0 (1H, dq, overlaps, J=12 and 6 Hz) and 4.3 (2H, dm, J=5 Hz) ppm.

EXAMPLE 3

The reaction was carried out in the same manner as described in the Example 2 except that $CF_3CH=CHCl$ was used in place of $CF_3CH=CHF$. $CF_3CH=CHOCH_2CH=CH_2$ was obtained in 50% yield.

EXAMPLE 4

Polymerization of $CF_3CH=CH(OCH_2CH=CH_2)$

Polymerization was conducted essentially the same way as described in *J. Polymer Sci. A: Polym. Chem* (1997) 35, 1593-1604.

To a clean vial containing a Teflon coated magnetic stirbar and a Teflon backed septa was added 15 mg (4.5×10$^{-5}$ mol) of $CO_2(CO)_8$ in an Argon-filled dry box. To this was added 2.6 mL of dry Toluene followed by 20 uL (1.1×10−4 mol) of dry diphenylsilane. This was mixed, and, after 15 minutes, the 1-allyloxy-3,3,3-trifluoropropene (0.65 mL, 5.0×10$^{-3}$ mol) was added via syringe. The vial was placed on a hot plate at 110° C. for 2 hrs while stirring. The reaction was quenched with a few drops of triethylamine (TEA) and then the polymer was precipitated in methanol. The polymer was then dried under vacuum at 80° C. for overnight.

The remaining polymer was determined by $^1$H, $^{19}$F NMR to contain the CH$_3$ groups in the main chain with characteristic broad peaks associated alkyl CH groups and phenyl silyl peaks as endgroups along with characteristic CF$_3$ groups. The resulting polymer was shown by GPC using polystyrene standards to have a MW=2,171 (weight average molecular weight) and Dp=3.01 (degree of polymerization).

EXAMPLE 5

Polymerization of $CF_3CH=C(OCH_2CH=CH_2)_2$

Polymerization is conducted in essentially the same manner as in Example 3, with the exception that $CF_3CH=C(OCH_2CH=CH_2)_2$ was used instead of 1-allyloxy-3,3,3-trifluoropropene.

The present invention has been described with particular reference to the preferred embodiments. It should be understood that variations and modifications thereof can be devised by those skilled in the art without departing from the spirit and scope of the present invention. Accordingly, the present invention embraces all such alternatives, modifications and variations that fall within the scope of the appended claims.

What is claimed is:

1. A process for the preparation of an allyloxytrifluoropropene derivative represented by the formula:

$CF_3CH=CR^1(OCH_2CR=CH_2)$ wherein:

R$^1$ is selected from the group consisting of: hydrogen, fluoro, and allyloxy group represented by the formula:

—$OCH_2CR=CH_2$ wherein R is selected from the group consisting of: hydrogen and methyl; and said process comprising the steps of:

contacting (i) a compound represented by the formula:

$CF_3CH=CR^2R^3$ wherein R$^2$ is selected from the group consisting of: hydrogen, chloro, and fluoro and wherein R$^3$ is chloro or fluoro; and (ii) an allyl alcohol derivative represented by the formula:

$HOCH_2CR=CH_2$ wherein R is selected from the group consisting of: hydrogen and methyl;

wherein said contacting is carried out in the presence of a base and optionally a solvent at a temperature and length of time sufficient to produce said allyloxytrifluoropropene derivative.

2. The process of claim 1, wherein R$^1$ is hydrogen.

3. The process of claim 1, wherein R$^1$ is an allyloxy group represented by the formula:

—$OCH_2CR=CH_2$ wherein R is hydrogen.

4. The process of claim 1, wherein R$^1$ is an allyloxy group represented by the formula:

—$OCH_2CR=CH_2$ wherein R is methyl.

5. The process of claim 1, wherein said allyloxytrifluoropropene derivative is a mixture comprising:

$CF_3CH=CF(OCH_2CR=CH_2)$ and $CF_3CH=C(OCH_2CR=CH_2)_2$ wherein R is selected from the group consisting of hydrogen and methyl.

6. The process of claim 1, wherein said allyloxytrifluoropropene derivative is selected from the group consisting of $CF_3CH=CH(OCH_2CH=CH_2)$ and $CF_3CH=C(OCH_2CH=CH_2)_2$.

7. The process of claim 1, wherein said allyloxytrifluoropropene derivative is selected from the group consisting of $CF_3CH=CH(OCH_2C(CH_3)=CH_2)$ and $CF_3CH=C(OCH_2C(CH_3)=CH_2)_2$.

8. The process of claim 1, wherein said compound represented by the formula $CF_3CH=CR^2R^3$ is selected from the group consisting of $CF_3CH=CHF$, $CF_3CH=CF_2$, and $CF_3CH=CHCl$.

9. The process of claim 8, wherein said compound represented by the formula $CF_3CH=CFR^3$ is $CF_3CH=CF_2$, wherein said contacting is carried out in a ratio of about 1:1 of said $CF_3CH=CF_2$ to said allyl alcohol derivative to produce an allyloxytrifluoropropene derivative represented by the formula:

$CF_3CH=CF(OCH_2CR=CH_2)$ wherein R is selected from the group consisting of: hydrogen and methyl.

10. The process of claim 8, wherein said compound represented by the formula $CF_3CH=CFR^3$ is $CF_3CH=CF_2$, wherein said contacting is carried out in a ratio of about 1:2 of said $CF_3CH=CF_2$ to said allyl alcohol derivative to produce an allyloxytrifluoropropene derivative represented by the formula:

$CF_3CH=C(OCH_2CR=CH_2)_2$ wherein R is selected from the group consisting of: hydrogen and methyl.

11. The process of claim 1, wherein said step of contacting is preferably carried out at a temperature from about 25° C. to about 50° C., at a pressure of about 0.5 atm to about 1 atm, and for a length of time from about 30 minutes to about 5 hours.

12. The process of claim 1, wherein said step of contacting is carried out at a temperature from about 25° C. to about 35° C., at a pressure from about 1 atm, and for a length of time from about 30 minutes to about 2 hours.

13. The process of claim 1, wherein R is hydrogen.

14. The process of claim 1, wherein R is methyl.

15. An allyloxytrifluoropropene derivative represented by the formula:

$$CF_3CH=C(OCH_2CH=CH_2)_2.$$

16. An allyloxytrifluoropropene derivative represented by the formula:

$$CF_3CH=C(OCH_2C(CH_3)=CH_2)_2.$$

17. An allyloxytrifluoropropene derivative represented by the formula:

$$CF_3CH=CH(OCH_2C(CH_3)=CH_2).$$

18. An allyloxytrifluoropropene derivative represented by the formula:

$$CF_3CH=CF(OCH_2CR=CH_2)$$

wherein R is selected from the group consisting of: hydrogen and methyl.

* * * * *